United States Patent
Bearnson (10) Patent No.: US 10,687,931 B2
(45) Date of Patent: Jun. 23, 2020

(54) BLOOD CLOT FILTER WITH LOCAL THROMBOLYTIC DRUG DELIVERY

(71) Applicant: HeartWare, Inc., Miami Lakes, FL (US)

(72) Inventor: Gill Brent Bearnson, Salt Lake City, UT (US)

(73) Assignee: HeartWare, Inc., Miami Lakes, FL (US)

( * ) Notice: Subject to any disclaimer, the term of this patent is extended or adjusted under 35 U.S.C. 154(b) by 315 days.

(21) Appl. No.: 15/586,675

(22) Filed: May 4, 2017

(65) Prior Publication Data

US 2017/0319321 A1 Nov. 9, 2017

Related U.S. Application Data

(60) Provisional application No. 62/332,609, filed on May 6, 2016.

(51) Int. Cl.
*A61F 2/01* (2006.01)
*A61M 5/172* (2006.01)

(52) U.S. Cl.
CPC ............ *A61F 2/01* (2013.01); *A61M 5/1723* (2013.01); *A61F 2002/016* (2013.01); *A61F 2230/0067* (2013.01); *A61F 2250/0023* (2013.01); *A61F 2250/0035* (2013.01); *A61F 2250/0067* (2013.01); *A61F 2250/0068* (2013.01); *A61M 2005/1726* (2013.01)

(58) Field of Classification Search
CPC ................. A61F 2/01; A61F 2002/016; A61F 2002/018; A61M 2005/1726
See application file for complete search history.

(56) References Cited

U.S. PATENT DOCUMENTS

| 4,405,688 | A | | 9/1983 | Lowery et al. |
| 5,053,008 | A | * | 10/1991 | Bajaj ................. A61F 2/01 604/104 |
| 5,713,853 | A | | 2/1998 | Clark et al. |
| 5,882,335 | A | | 3/1999 | Leone et al. |
| 8,574,259 | B2 | | 11/2013 | Welch et al. |

(Continued)

FOREIGN PATENT DOCUMENTS

| CN | 103961191 A | 8/2014 |
| CN | 104707181 A | 6/2015 |

OTHER PUBLICATIONS

International Search Report and Written Opinion dated Jul. 6, 2017, for corresponding International Application No. PCT/US2017/031017; International Filing Date: May 4, 2017 consisting of 11-pages.

(Continued)

*Primary Examiner* — Lauren P Farrar
*Assistant Examiner* — James D Ponton
(74) *Attorney, Agent, or Firm* — Christopher & Weisberg, P.A.

(57) ABSTRACT

A thrombus capture and lysis device including a filter sized to be implanted within a blood vessel. The filter includes a plurality of hollow elements defining a mesh sized to span an area of the blood vessel. Each of the plurality of hollow elements defines a plurality of pores being sized to allow passage of a thrombolytic drug out through the pores and to prevent a thrombus forming component from entering the pores.

18 Claims, 5 Drawing Sheets

(56) References Cited

U.S. PATENT DOCUMENTS

| | | |
|---|---|---|
| 2002/0165575 A1 | 11/2002 | Saleh |
| 2003/0109824 A1* | 6/2003 | Anderson ............... A61F 2/013 604/104 |
| 2003/0176884 A1* | 9/2003 | Berrada ................. A61F 2/013 606/200 |
| 2004/0116960 A1* | 6/2004 | Demond ............. A61B 17/221 606/200 |
| 2005/0085847 A1* | 4/2005 | Galdonik .................. A61F 2/01 606/200 |
| 2006/0047300 A1* | 3/2006 | Eidenschink ............ A61F 2/01 606/200 |
| 2006/0069405 A1 | 3/2006 | Schaeffer et al. |
| 2007/0225634 A1* | 9/2007 | Ferren ................ A61B 1/00156 604/27 |
| 2011/0106136 A1 | 5/2011 | Thompson et al. |
| 2012/0216914 A1 | 8/2012 | Pacetti |
| 2014/0288588 A1* | 9/2014 | Lam ....................... A61F 2/013 606/200 |

OTHER PUBLICATIONS

Erickson, Harold P., Size and Shape of Protein Molecules at the Nanometer Level Determined by Sedimentation, Gel Filtration, and Electron Microscopy, Shulin Li (ed.), Biological Procedures Online, vol. 11, No. 1.

China National Intellectual Property Adminstration, Notice on the First Office Action, Dated Nov. 13, 2019, for corresponding Chinese Application No. 201780027814.6, 19 pages.

\* cited by examiner

BLOOD CLOT FILTER WITH LOCAL THROMBOLYTIC DRUG DELIVERY

CROSS-REFERENCE TO RELATED APPLICATION

This application is related to and claims priority to U.S. Provisional Patent Application Ser. No. 62/332,609, filed May 6, 2016, entitled BLOOD CLOT FILTER WITH LOCAL THROMBOLYTIC DRUG DELIVERY, the entirety of which is incorporated herein by reference.

STATEMENT REGARDING FEDERALLY SPONSORED RESEARCH OR DEVELOPMENT n/a

TECHNICAL FIELD

The present disclosure relates to an indwelling blood clot filter that catches a blood clot, also referred to as thrombus, in flowing blood.

BACKGROUND

Filters can be placed in blood vessels to catch thrombus carried in the flowing blood. Such filters have been used clinically for many years. Filters are primarily placed temporarily during a high-risk procedure. One of the problems with long-term placement of a clot filter is what happens to the thrombus after the clot thrombus been caught in the filter. Where a filter is placed temporarily, the thrombus typically is removed by removing the filter. However, a long-term indwelling filter is not easily removed.

Blood clots can be dissolved in patients that develop them; however, this is done with significant risk to the patient when aggressive thrombolytic drugs are used. Among the risks is the possibility that the clot can move to the brain and cause a stroke, or move to other parts of the body and result in an embolism. Thrombolytic drugs can be administered to the patient, and are sometimes effective in dissolving a clot in place. However, the thrombolytic drug enters the patient's bloodstream and thus can create a risk of a bleeding event, such as a hemorrhagic stroke.

SUMMARY

The present application advantageously provides for a thrombus capture and lysis device including a filter sized to be implanted within a blood vessel. The filter includes a plurality of hollow elements defining a mesh sized to span an area of the blood vessel. Each of the plurality of hollow elements defines a plurality of pores being sized to allow passage of a thrombolytic drug out through the plurality of pores and to prevent a thrombus forming component from entering the plurality pores.

In another aspect of this embodiment, each of the plurality of hollow elements are in fluid communication with each other.

In another aspect of this embodiment, the device includes a dispenser configured dispense the thrombolytic drug, the dispenser being in fluid communication with the plurality of hollow elements.

In another aspect of this embodiment, the plurality of hollow elements defines a substantially conical shape.

In another aspect of this embodiment, the plurality of hollow elements defines an oblique angle.

In another aspect of this embodiment, the mesh defines a plurality of gaps between adjacent hollow elements, wherein each gap defines a diameter, the diameter of the gap being smaller than a diameter of the thrombus forming components.

In another aspect of this embodiment, the filter includes a first surface and an opposite second surface, and wherein the plurality of pores are entirely disposed on the first surface.

In another aspect of this embodiment, the filter includes a first portion and a second portion, and wherein the second portion is configured to be positioned downstream of the first portion when the filter is implanted within the blood vessel, and where in the second portion includes at least one from the group consisting of more pores, larger pores, and both larger pores and more pores than the first portion.

In another aspect of this embodiment, the thrombus forming component is fibrinogen.

In another aspect of this embodiment, the thrombolytic drug is tissue plasminogen activator.

In another aspect of this embodiment, the plurality the pores have an average pore size of between 5 and 10 nm.

In another embodiment, a thrombus capture and lysis device includes a filter sized to be implanted within a blood vessel. The filter includes a plurality of hollow elements defining a mesh sized to span an area of the blood vessel. Each of the plurality of hollow elements defines a plurality of pores, the plurality of pores being sized to allow passage of a thrombolytic drug out through the plurality of pores and to prevent a thrombus forming component from entering the plurality of pores. A plurality of sensors coupled to the filter are included, the plurality of sensors being configured to detect the presence of the thrombus forming component and to initiate a release of the thrombolytic drug.

In another aspect of this embodiment, the device includes a dispenser in fluid communication with the hollow elements and in communication with the plurality of sensors, the dispenser retaining a volume of the thrombolytic drug.

In another aspect of this embodiment, the dispenser includes a plurality of selectively operable microdispensers disposed at different locations on the filter.

In another aspect of this embodiment, the device includes a control circuit operatively connected to the plurality of sensors and microdispensers, the control circuit being operative to actuate a respective microdispenser proximate a respective one of the plurality of sensors when the presence of thrombus forming component is detected by the respective one of the plurality of sensors.

In another aspect of this embodiment, the filter includes a first surface and an opposite second surface, and wherein the plurality of pores are entirely disposed on the first surface.

In another aspect of this embodiment, the filter includes a first portion and a second portion, and wherein the second portion is configured to be positioned downstream of the first portion when the filter is implanted within the blood vessel, and where in the second portion includes at least one from the group consisting of more pores, larger pores, and both larger pores and more pores than the first portion.

In another aspect of this embodiment, the thrombus forming component is fibrinogen.

In another aspect of this embodiment, the thrombolytic drug is tissue plasminogen activator.

In yet another embodiment, a thrombus capture and lysis device includes a filter sized to be implanted within a blood vessel. The filter includes a plurality of hollow elements defining a mesh sized to span an area of the blood vessel. Each of the plurality of hollow elements defining a plurality of pores. The plurality of pours being sized to allow passage of a thrombolytic drug out through the plurality of pores and to prevent fibrinogen from entering the plurality of pores. The filter includes a first portion and a second portion, and the second portion is configured to be positioned downstream of the first portion when the filter is implanted within the blood vessel, and the second portion includes at least one from the group consisting of more pores, larger pores, and both larger pores and more pores than the first portion. The filter further includes a first surface and an opposite second surface, and the plurality of pores are entirely disposed on the first surface. A plurality of sensors is coupled to the first surface of the filter at a plurality of different locations. The plurality of sensors being configured to detect the presence of fibrinogen and to initiate a release of the thrombolytic drug. A plurality of selectively operable microdispensers are in fluid communication with the hollow elements and in communication with the plurality of sensors, the plurality of microdispensers retaining a volume of the thrombolytic drug. A control circuit is operatively connected to the plurality of sensors and microdispensers, the control circuit being operative to actuate a respective microdispenser proximate a respective one of the plurality of sensors when the presence of fibrinogen is detected by the respective one of the plurality of sensors.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figures 1, 2:
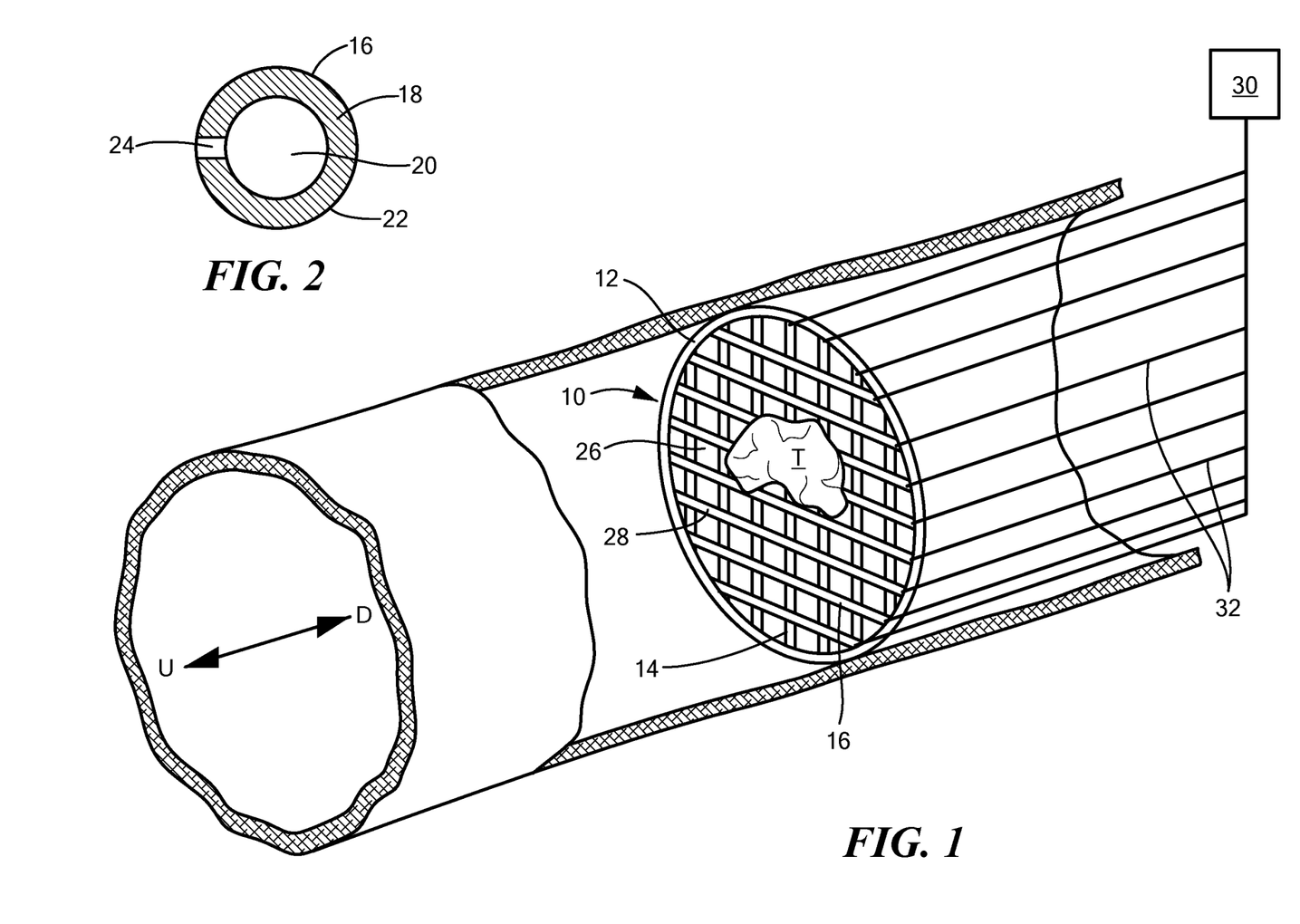
FIG. 1 is side insider view an exemplary thrombus capture and lysis device constructed in accordance with the principles of the present application and implanted within a blood vessel.
FIG. 2 is cross-section view of a hollow element of the filter of the device shown in FIG. 1.

Referring now to the drawings in which like reference designators refer to like elements, there is shown in FIG. 1 an exemplary thrombus capture and lysis device constructed in accordance with the principles of the present application and designated generally as "10." The device 10 includes anchoring element 12 adapted to hold the structure in place within a blood vessel, shown in FIG. 1 with portions removed for clarity of illustration. The anchoring element 12 is depicted schematically as a simple ring, but in practice the anchoring element 12 may include devices such as are commonly used for anchoring other intravascular devices such as stents, filters, sutures, barbs, and the like. The device 10 further includes a filter 14 sized to span the inner area of the particular blood vessel in which the device is implanted. The filter 14 includes a plurality of hollow elements 16 that cooperate to define a mesh or mesh-like structure. In such a configuration, each hollow element 16 may be in the form of an elongated, hollow fiber. As best seen FIG. 2, each hollow element 16 includes a wall 18, which may be in the form of a membrane surrounding and defining an interior space 20 within the hollow element 16. The wall 18 also defines an exterior surface 22 of each of the hollow elements. The walls 18 of the respective hollow elements 18 include a plurality of pores 24, extending through the walls 18 and communicating with the interior space 20 and the exterior surface 22. The hollow elements 16 are arrayed and interconnected within filter 14 to form gaps 26 interspersed with the hollow elements 16. Gaps 26 have dimensions larger than the dimensions of blood cells, so that blood can pass through the gaps 26. The particular grid or mesh-like arrangement of the hollow elements 16 shown in FIG. 1 is merely for illustrative purposes. The filter 14 is mechanically connected to the anchoring element 12. In some embodiments, the hollow elements 16 of the filter 14 may form part or all of the anchoring element 12.

The filter 14 as a whole defines a front surface 28, which is the surface of the filter 14 facing toward the viewer in FIG. 1. The front surface 28 of the filter 14 as referred to herein is the surface that first encounters the flowing blood when the device 10 is implanted within a blood vessel. The anchoring element 12 and filter 14 are adapted for implantation within a blood vessel, most commonly a vein such as a vena cava, although the device 10 may be implanted within any blood vessel. In one configuration, device 10 as a whole is arranged so that it can be collapsed to a relatively small diameter for implantation by advancing it through the circulatory system using a catheter and then expanded to the operative, implanted condition shown in FIG. 1. The blood vessel has a normal direction of blood flow, referred to herein as the downstream direction, and is shown by arrow D. The anchoring element 12 is arranged so that in the implanted condition depicted in FIG. 1, the front surface 28 of the filter faces generally in the upstream direction, indicated by arrow U in FIG. 1.

The interior spaces 20 within some or all of the hollow elements 18 are connected in communication with a source of a thrombolytic drug 30 (FIG. 1) through connecting elements 32 depicted schematically. For example, in this embodiment the thrombolytic drug source 30 may include an injection port disposed adjacent the patient's skin such that a liquid including the thrombolytic drug can be injected into the port, or may be an implantable pump connected to an implantable reservoir filled with a thrombolytic drug. The connecting elements may include any type of implantable fluid conduits and manifolds. Also, the interior spaces 20 may be interconnected with one another, so that some of the fibers serve as interconnecting elements for other fibers. At the ends of hollow elements 16 remote from their connections to connecting elements 32, the interior space 20 is closed off.

In one configuration, the pores 24 (FIG. 2) in the walls or membranes 18 of the hollow elements 16 are arranged so as to allow passage of the thrombolytic drug from the interior space 20 of the hollow elements 16 to the exterior surface 22, but to block passage of at least one thrombus-forming constituent of blood from the exterior surface 22 into the interior space 20. This limits or precludes thrombus formation within the interior spaces 20 of the hollow elements 16 when the thrombolytic drug is not present in those spaces. In one arrangement, the pores 24 have a size that is larger than the diameter of the thrombolytic drug but smaller than the size of thrombus-forming constituents.

One common thrombolytic drug is tissue plasminogen activator ("tPA"). tPA is a protein having a mass of 72 kilo Daltons and having a globular form. The estimated diameter of the tPA molecule is 5.5 nm, based on the relationship $$\text{Radius}_{min} = 0.066 \, m^{1/3} \quad \text{(Formula 1)}$$

where m is the mass of the protein in Daltons, $\text{Radius}_{min}$ is the radius of the protein molecule in nm. This relationship assumes that the protein molecule has a spherical configuration, which is reasonable given its globular form.

The estimating technique set forth in Formula 1, and other techniques for estimating and measuring the size of protein molecules are known in the art. See Erickson H. P., Size and Shape of Protein Molecules at the Nanometer Level Determined by Sedimentation, Gel Filtration, and Electron Microscopy, Shulin Li (ed.), Biological Procedures Online, Volume 11, Number 1 (2009), the disclosure of which is incorporated herein by reference. Fibrinogen, a thrombus-forming molecule present in blood, has an atomic mass of 340 kilo Daltons. Based on the relationship set forth in Formula 1 above, the fibrinogen molecule has an estimated diameter of 9.21 nm. Thus, to permit passage of tPA but block passage of fibrinogen, the pore 24 size should be between 5.5 nm and 9.2 nm, and in some configurations between 5 and 10 nm. Platelets, another constituent of blood involved in thrombus formation, are cell fragments having an average diameter of 2 μm, i.e., 2000 nm. Thus, a pore 24 size between 5.5 nm and 2000 nm would permit passage of tPA but block passage of platelets. One method of making hollow fibers with pore sizes as small as 5 nm is disclosed in U.S. Pat. No. 4,405,688, the disclosure of which is incorporated herein as a part of this disclosure. The appropriate pore 24 size for use with thrombolytic drugs other than tPA can be estimated in a similar manner using the technique of Formula 1 or other known estimating or measuring techniques. Any thrombolytic drug can be used. Common thrombolytic drugs include anistreplase, streptokinase, kabikinase, urokinase, reteplase, tenecteplase, and rokinase, as well as tPA. One thrombolytic drug, or a combination of thrombolytic drugs may be used. The hollow elements 16 can be formed from polymeric materials compatible with blood, as, for example, polyolefins such as polymethylpentene and polypropylene. These materials have been used in contact with blood in devices such as oxygenators.

In a method of operation according to a further embodiment of the disclosure, the device 10 is implanted in the blood vessel and connected to the source of tPA or other thrombolytic drug as discussed above. While the device 10 is in place, blood passes through gaps 26 in the filter 14 and flows in the downstream direction. Thrombus T, carried by the blood, may deposit on filter 14, abutting the outer surfaces 22 of the hollow elements 16. Source 30 may be actuated to deliver the thrombolytic drug at slow, steady rate, or may be actuated periodically. The thrombolytic drug passing out of the pores 24 in the vicinity of the clot contacts the clot at or near the interface between the clot and the hollow element 16, and thus dissolves the clot from the bottom up.

In a further embodiment of the disclosure, the walls 18 of the fibers or other hollow elements can be formed as solid membranes, without discrete pores 24. The membrane material is selected so that it is permeable to the thrombolytic drug. The thrombolytic drug will move through the membrane in a diffusion process driven by osmotic pressure, fluid pressure maintained in the interior spaces of the hollow elements 16, or both. The material of the membrane may be selected to have greater permeability to the thrombolytic drug than to thrombus-forming constituents of the blood.

Figure 3:
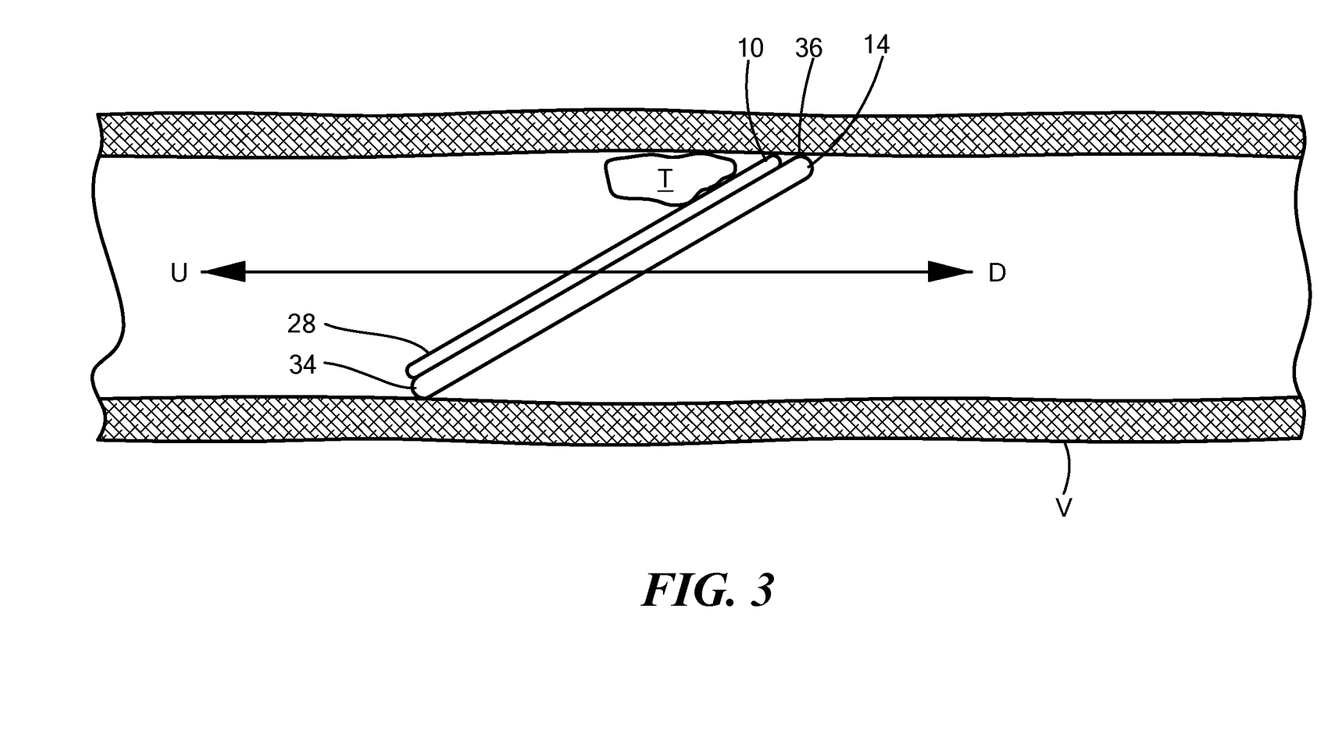
FIG. 3 is a side-cross sectional of the device shown in FIG. 1 implanted at an oblique angle within the blood vessel.

Referring now to FIG. 3, in another configuration, the anchoring element 12 and filter 14 are configured so that when the device 10 is implanted in the blood vessel V, the front surface 28 of the filter 14, which faces generally towards the upstream direction of the vessel, is oblique to the upstream and downstream directions. Stated another way, the front surface of the filter is oblique to the central axis of the blood vessel. Thus, a first portion 34 of the filter 14 front surface 28 is disposed upstream of a second portion 36 of the front surface 28. The downstream flow of blood within the vessel tends to displace thrombus deposited on the front surface 28 of the filter 14 downstream, toward the second or downstream section of the front surface 28. As discussed above with reference to FIG. 1, the filter 14 includes hollow elements 16 such as fibers, and the interior spaces 20 of at least some of the fibers are connected to a source of thrombolytic drug. In one configuration, the fibers of the filter 14, the connections 32 to the thrombolytic drug supply 30, or both, are arranged so that the thrombolytic drug will be applied in proximity to the second portion 36. For example, the fibers in and proximate the second portion 36 may have more pores, or larger pores, than the fibers in and near the first portion 34. Some of the fibers in the first section may be non-porous, and may be solid fibers with no interior spaces. Some of the fibers in the first portion may not be connected to the source of thrombolytic drug, or may have restricted connections to slow the passage of thrombolytic drug to such fibers. Because the thrombolytic drug is applied preferentially in regions of the filter most likely to collect thrombus, it is used more efficiently. Thus, the total dose of thrombolytic drug administered to the patient can be reduced.

Figure 4:
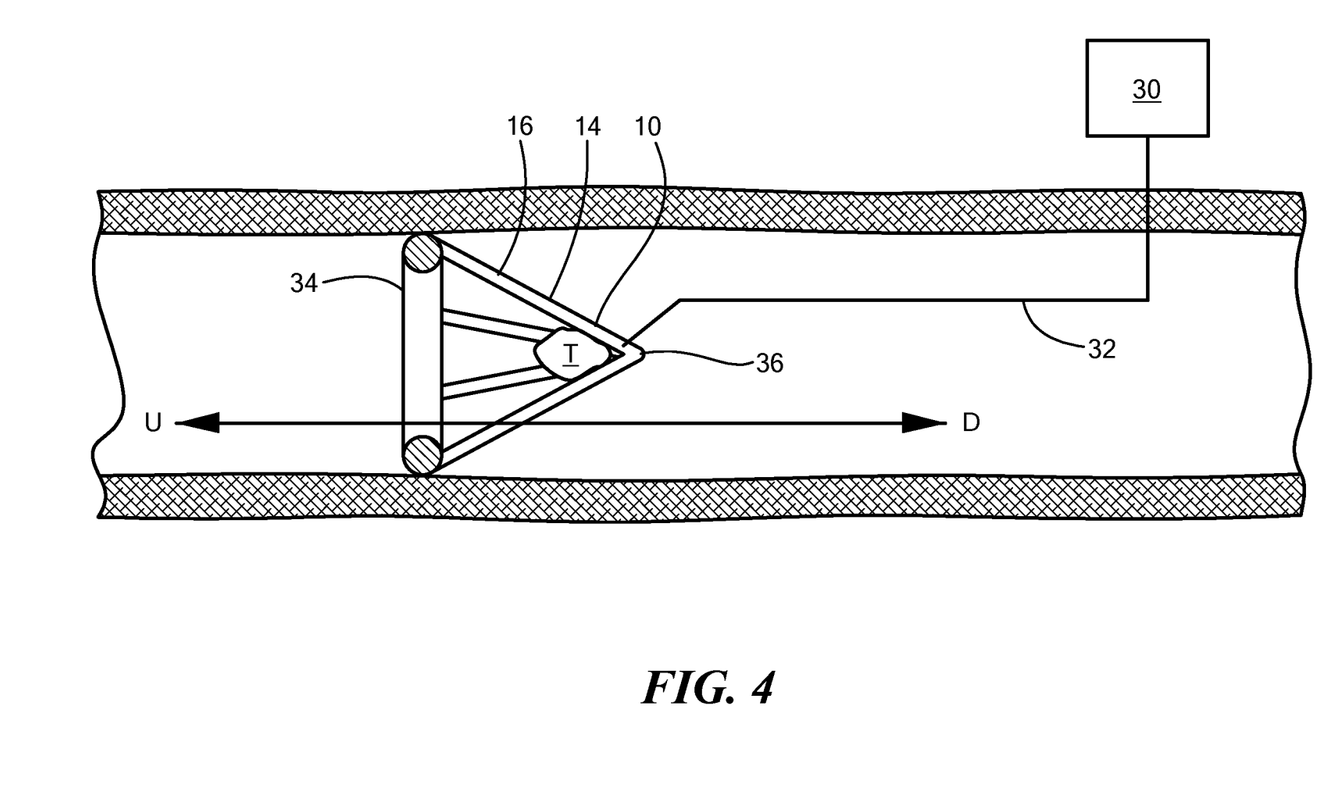
FIG. 4 is a cross-sectional view of another thrombus capture and lysis device constructed in accordance with the principles of the present application and implanted within a blood vessel.

Referring now to FIG. 4, in another configuration, the filter 14, or at least the front surface 28 of the filter 14, may be generally conical in shape, so that the base of the cone forms the first or upstream portion 34 of the filter front surface 28 and the portion of the filter front surface adjacent the apex of the cone forms the second or downstream portion 36. The hollow elements 16, the connections 32 to the drug source 30, or both, are configured to that the drug is delivered preferentially adjacent the downstream portion 36. In further variants (not shown) the front surface of the filter 14 may include multiple depressions or valleys forming the downstream or second portion of the front surface.

As discussed above, it is advantageous to deliver the drug through the hollow elements 16 constituting the filter 14. However, in other embodiments, the drug may be delivered in proximity to the filter 14 by other methods and structures. For example, the drug 30 source may be connected to a tubular element (not shown) having a single outlet port, or a small number of outlet ports, upstream of the filter front surface, or within the filter.

Figure 5:
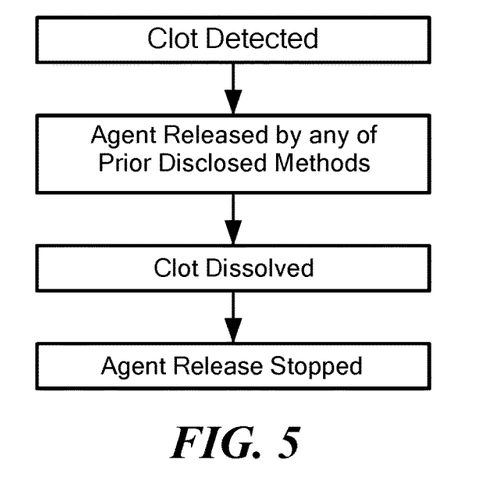
FIG. 5 is a flow chart illustrating a method of thrombus capture and lysis accordance the present application.

According to a further aspect of the disclosure, the thrombolytic drug can be delivered in response to detection of thrombus accumulated on the filter. This arrangement is shown in the flow chart of FIG. 5. Detection of a clot can be performed by an imaging modality such as magnetic resonance imaging of the filter or by a non-imaging modality such as measurement of a pressure differential between the upstream and downstream sides of the filter. The source of thrombolytic drug can be actuated automatically or manually to start release in response to clot detection and to cease release when the clot has dissolved completely or partially. The filter itself may incorporate one or more sensors capable of detecting thrombus. For example, upstream and downstream pressure sensors such as small piezoelectric sensors (not shown) can be built into the filter or the anchoring structure, and can be connect by wired or wireless connections to a control circuit (not shown) linked to the drug source.

Figure 6:
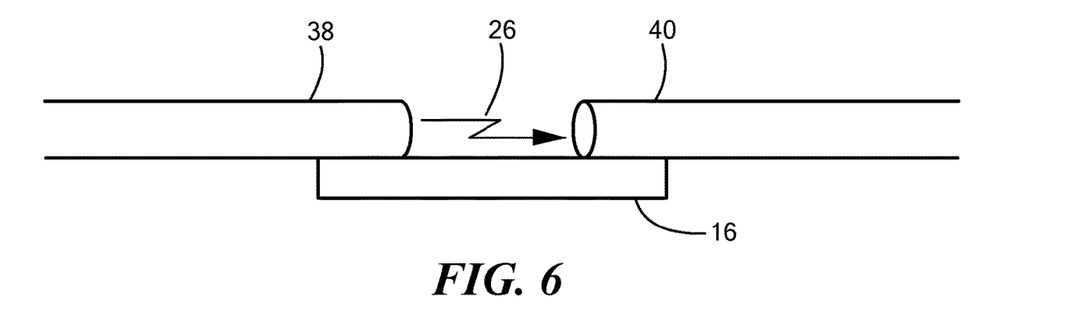
FIG. 6 is a side view of a portion of another thrombus capture and lysis device constructed in accordance with the principles of the present application.
Figure 7:
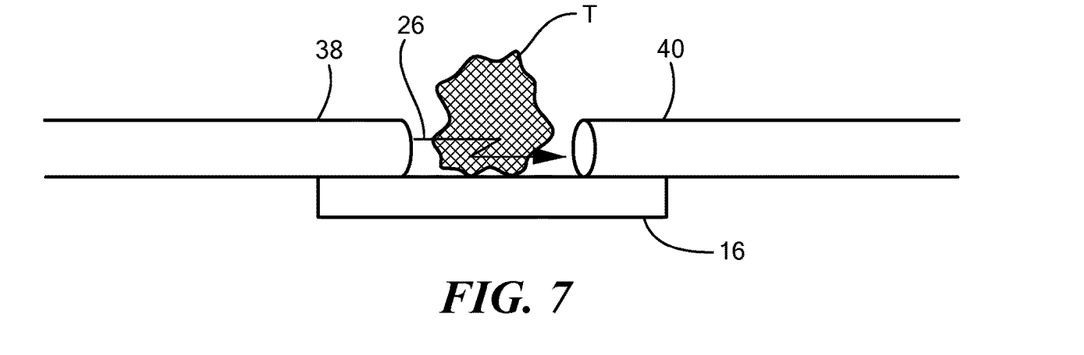
FIG. 7 is side view of FIG. 6 with thrombus deposed between the two optical sensor elements shown in FIG. 6.

Referring now to FIGS. 6 and 7, in another configuration, localized sensors can be provided that detect the presence of thrombus at or near a particular location of the filter. For example, an optical sensor may include a pair of optical elements such as the ends of two optical fibers 38 and 40 mounted to an underlying structure such as one of the hollow elements 16 constituting the filter 14 with a gap 26 between the optical elements so that light from one of the optical elements can propagate across the gap 26 into the other one of the optical elements. The optical transmission or optical absorption of light transmitted through the gap may vary depending upon whether thrombus T is absent (FIG. 6) or presence (FIG. 7). In place of optical fibers, the optical elements may include an emitter such as a light emitting diode ("LED") and a receiver such as a photodiode or phototransistor arranged to convert received light to electrical signals.

Figure 8:
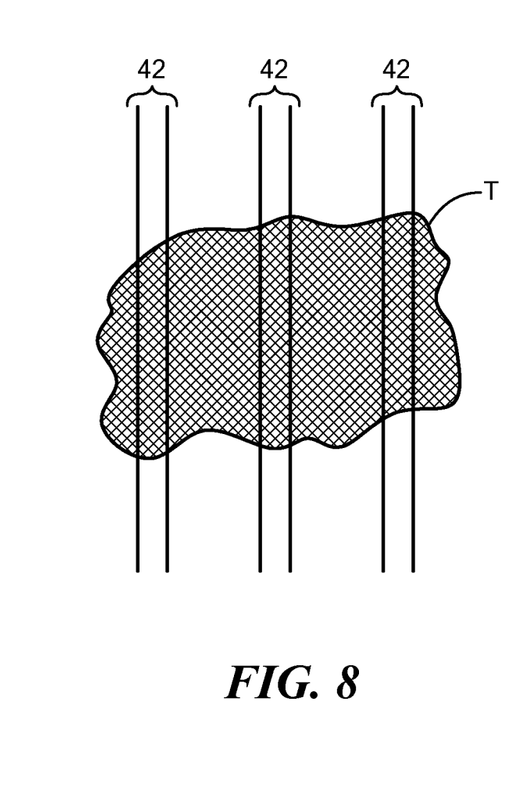
FIG. 8 is a front view of a portion of another thrombus capture and lysis device constructed in accordance with the principles of the present application.

Referring now to FIG. 8, in another configuration, electrically conductive elements 42 are disposed in proximity to one another within or on the filter. For example, the conductive elements 42 may be incorporated within the individual fibers 16 of the filter 14. Thrombus T present on or between these elements 42 causes a change in the electrical impedance between the elements or a change in capacitance between the conductive elements. Other forms of sensors include microelectromechanical or "MEMS" sensors. For example, a MEMS sensor may incorporate an element exposed to the blood and electromechanical elements for driving the element in vibration and detecting its response. Deposition of thrombus on the element may change the mechanical resonant properties of the element, such as its resonant frequency or degree of damping.

Figure 9:
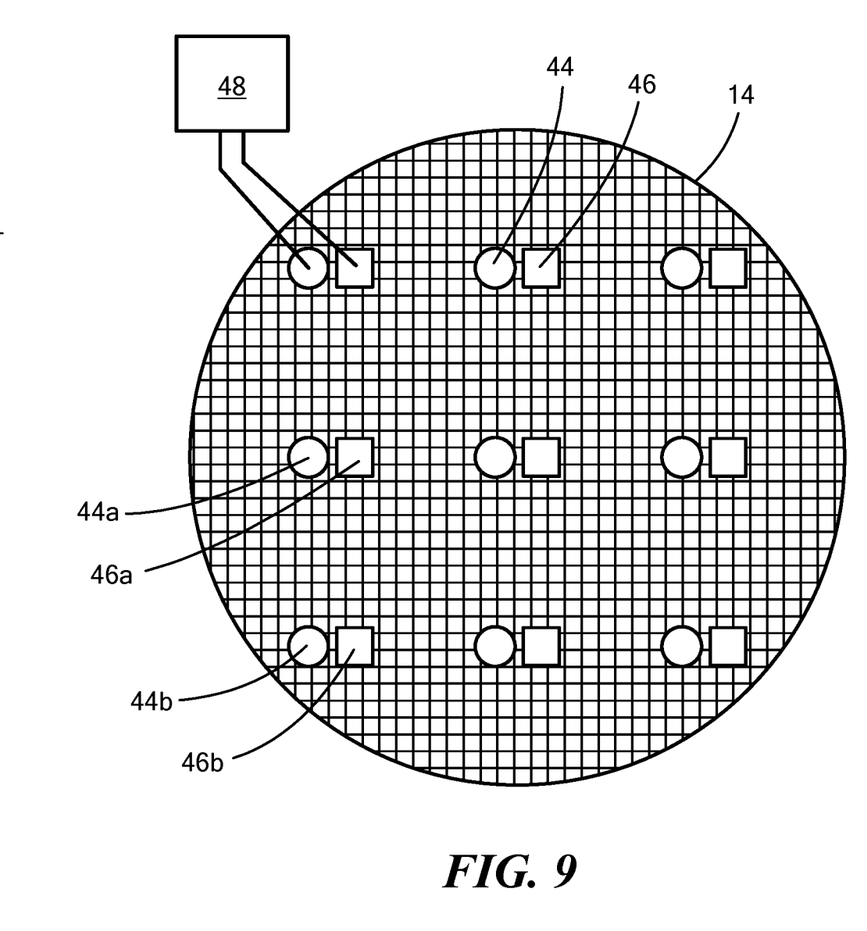
FIG. 9 is a top view of a filter constructed in accordance with present application including a MEMS device including microdispensers and sensor.

Referring now to FIG. 9, localized sensors may be used in conjunction with localized micro drug dispensers. Small MEMS drug dispensers are known in the art. Such dispensers can be actuated selectively by an electrical signal to dispense a drug from a small reservoir included in the dispenser itself. A structure according to a further aspect of the disclosure may include filter 14 with localized sensors 44 disposed at various locations on or in the filter 14. A micro dispenser 46 is disposed on or in the filter 14 adjacent each sensor 14. The dispensers 46 and sensors 44 are operatively connected to a control circuit 48. The control circuit 48 is configured to respond to detection of thrombus at a particular sensor 44 by actuating a particular dispenser 46 disposed in proximity to that sensor 44 to release thrombolytic drug. For example, if sensor 44a detects thrombus, dispenser 46a is actuated. If sensor 44b detects thrombus, dispenser 46b is actuated, and so on. The dispensers and sensors need not be present in a paired arrangement as shown. For example, each sensor may be associated with plural dispensers, or vice-versa. The dispensers need not have reservoirs. For example, a localized dispenser can include an outlet port, or pores of an individual fiber, connected to a remote drug supply. The control circuit 48 may control the remote drug supply or the connections between the remote drug supply and the individual ports. In this arrangement, the thrombolytic drug is dispensed where needed and when needed, so thus further reducing the amount of drug that must be introduced into the patient's body to keep the filter clear of thrombus.

In the discussion above, devices according to certain aspects of the present disclosure have been referred to as intravascular devices, and have been described as implanted within blood vessels. However, devices according to the present disclosure also can be installed in prosthetic devices that form part of the circulatory system as and carry flowing blood. For example, filters 14 according to the present disclosure may be installed in or on blood-carrying passages of devices such as blood pumps used as elements of mechanical circulatory support devices, also referred to as ventricular assist devices or "VADs", or in conduits used to connect such pumps to the native circulatory system of the patient. In such an arrangement, the structure used to mount the filter may be arranged for attachment to the prosthetic device, or may be part of the prosthetic device itself. Further, filters 14 according to the present disclosure may be mounted within the heart itself. The term "circulatory element" as used herein includes both natural blood vessels and the heart, as well as passages or chambers of a prosthetic device that, when installed, forms a part of the circulatory system.

What is claimed is:

1. A thrombus capture and lysis device, comprising: a filter sized to be implanted within a blood vessel, the filter including a first upstream portion and a second downstream portion, both portions being configured to be in contact with a wall of the blood vessel at an oblique angle when the filter is implanted within the blood vessel, the filter further including a plurality of hollow elements defining a mesh sized to span an area of the blood vessel and an anchoring element, the anchoring element being entirely defined by the plurality of hollow elements, each of the plurality of hollow elements defining a plurality of pores, the plurality of pores being sized to allow passage of a thrombolytic drug out through the plurality of pores and to prevent a thrombus forming component from entering the plurality of pores, the filter further defining a planar first surface configured to face an upstream direction of the blood vessel and an opposite second surface, the plurality of pores being entirely disposed on the planar first surface.

2. The device of claim 1, wherein each of the plurality of hollow elements are in fluid communication with each other.

3. The device of claim 1, further including a dispenser configured to dispense the thrombolytic drug, the dispenser being in fluid communication with the plurality of hollow elements.

4. The device of claim 1, wherein the plurality of hollow elements defines a substantially conical shape.

5. The device of claim 1, wherein the plurality of hollow elements defines a second oblique angle.

6. The device of claim 1, wherein the mesh defines a plurality of gaps between each adjacent hollow element of the plurality of hollow elements, wherein each gap defines a diameter, the diameter of the gap being smaller than a diameter of the thrombus forming components.

7. The device of claim 1, wherein the second downstream portion includes at least one from the group consisting of more pores, larger pores, and both larger pores and more pores than the first upstream portion.

8. The device of claim 1, wherein the thrombus forming component is fibrinogen.

9. The device of claim 1, wherein the thrombolytic drug is tissue plasminogen activator.

10. The device of claim 1, wherein the plurality of pores have an average pore diameter of between 5 and 10 nm.

11. A thrombus capture and lysis device, comprising:
a filter sized to be implanted within a blood vessel, the filter including a first upstream portion and a second downstream portion, both portions being configured to be in contact with a of the blood vessel at an oblique angle when the filter is implanted within the blood vessel, the filter further including a plurality of hollow elements defining a mesh sized to span an area of the blood vessel and an anchoring element, the anchoring element being entirely defined by the plurality of hollow elements, each of the plurality of hollow elements defining a plurality of pores, the plurality of pores being sized to allow passage of a thrombolytic drug out through the plurality of pores and to prevent a thrombus forming component from entering the plurality of pores, the filter further defining a planar first surface configured to face an upstream direction of the blood vessel and an opposite second surface, the plurality of pores being entirely disposed on the planar first surface; and a plurality of sensors coupled to the filter, the plurality of sensors being configured to detect a presence of the thrombus forming component and to initiate a release of the thrombolytic drug.

12. The device of claim 11, further including a dispenser in fluid communication with the hollow elements and in communication with the plurality of sensors, the dispenser retaining a volume of the thrombolytic drug.

13. The device of claim 12, wherein the dispenser includes a plurality of selectively operable microdispensers disposed at different locations on the filter.

14. The device of claim 13, further comprising a control circuit operatively connected to the plurality of sensors and the plurality of microdispensers, the control circuit being operative to actuate a respective microdispenser proximate a respective one of the plurality of sensors when the presence of thrombus forming component is detected by the respective one of the plurality of sensors.

15. The device of claim 11, wherein the filter includes a first surface and an opposite second surface, and wherein the plurality of pores are entirely disposed on the first surface.

16. The device of claim 11, wherein the thrombus forming component is fibrinogen.

17. The device of claim 11, wherein the thrombolytic drug is tissue plasminogen activator.

18. A thrombus capture and lysis device, comprising:
a filter sized to be implanted within a blood vessel, the filter including a plurality of hollow elements defining a mesh sized to span an area of the blood vessel and an anchoring element, the anchoring element being entirely defined by the plurality of hollow elements, each of the plurality of hollow elements defining a plurality of pores, the plurality of pores being sized to allow passage of a thrombolytic drug out through the plurality of pores and to prevent fibrinogen from entering the plurality of pores, the filter further defining a planar first surface configured to face an upstream direction of the blood vessel and an opposite second surface, the plurality of pores being entirely disposed on the planar first surface;

the filter including a first upstream portion and a second downstream portion, both portions being configured to be in contact with a wall of the blood vessel at an oblique angle when the filter is implanted within the blood vessel, and the second portion includes at least one from the group consisting of more pores, larger pores, and both larger pores and more pores than the first portion;

a plurality of sensors coupled to the first surface of the filter at a plurality of different locations, the plurality of sensors being configured to detect a presence of fibrinogen and to initiate a release of the thrombolytic drug;

a plurality of selectively operable microdispensers in fluid communication with the hollow elements and in communication with the plurality of sensors, the plurality of microdispensers retaining a volume of the thrombolytic drug; and a control circuit operatively connected to the plurality of sensors and microdispensers, the control circuit being operative to actuate a respective microdispenser proximate a respective one of the plurality of sensors when the presence of fibrinogen is detected by the respective one of the plurality of sensors.

* * * * *